United States Patent [19]

Sunstein et al.

[11] Patent Number: 4,856,906

[45] Date of Patent: Aug. 15, 1989

[54] ENHANCED SYSTEM FOR TRANSMISSION LOSS COMPARISON

[75] Inventors: Drew E. Sunstein, Hollis; Clifford D. Caseley, Hudson, both of N.H.

[73] Assignee: Circuits and Systems, Inc., Amherst, N.H.

[21] Appl. No.: 93,929

[22] Filed: Sep. 8, 1987

Related U.S. Application Data

[63] Continuation-in-part of Ser. No. 912,953, Sep. 29, 1986, Pat. No. 4,759,631.

[51] Int. Cl.$^4$ ............................................. G01N 21/00
[52] U.S. Cl. ..................... 356/435; 356/436; 250/354.1
[58] Field of Search ................ 356/435, 436; 250/565, 250/575, 345, 354.1

[56] References Cited

U.S. PATENT DOCUMENTS

| | | | |
|---|---|---|---|
| 2,452,122 | 10/1948 | Gumaer | 250/354.1 |
| 3,180,984 | 4/1965 | Fertig et al. | 250/354.1 |
| 3,822,097 | 7/1974 | Allington | 356/435 |
| 3,979,589 | 7/1976 | Sternberg et al. | 250/345 |
| 3,989,382 | 11/1976 | Kent | 356/435 |
| 4,047,815 | 9/1977 | Sedlacek | 250/565 |
| 4,525,069 | 6/1985 | Tanaka et al. | 356/435 |
| 4,673,812 | 6/1987 | Yomeda | 252/345 |

Primary Examiner—Bruce C. Anderson
Attorney, Agent, or Firm—Bromberg & Sunstein

[57] ABSTRACT

The present invention provides a system for transmission loss comparison.

On embodiment of the present invention compares the transmission losses through optical paths through a first solution and a second solution. This embodiment includes first and second light sources for transmitting light through the first and second solutions. Also provided are first and second light detectors corresponding to the first and second light sources, and comparison means for comparing the outputs of the two detectors in order to determine which solution is darker.

In addition, this embodiment includes a common gain balance configuration means for calibrating the relative gain of the two light detectors in order to compensate for signal differences between each source/detector path arising from various mechanical or optical factors. Further included is a dark solution compensation bias to compensate for differences between each source/detector path arising from spectral differences between the two light sources.

In order to stabilize the measurement decision, the system also provides source modulation hysteresis, wherein a feedback path is provided between the output of the comparison means and one of the light sources.

18 Claims, 2 Drawing Sheets

ENHANCED SYSTEM FOR TRANSMISSION LOSS COMPARISON

CROSS-REFERENCE TO RELATED APPLICATIONS

This is a continuation-in-part of co-pending U.S. application Ser. No. 912,953, filed on Sept. 29, 1986, now U.S. Pat. No. 4,759,631, which is incorporated herein by reference.

BACKGROUND OF THE INVENTION

1. Field of the Invention

The present invention pertains to systems for comparing transmission losses, especially through optical transmission paths, although the invention has application to other types of transmission paths.

2. Description of Related Art

Systems for comparing transmission losses through alternative paths are well known in the art. One prior art optical comparison device employs a split common light source to transmit light along a given path through each of a corresponding pair of samples. The transmitted light is monitored by a corresponding pair of light receivers. The output of the light receivers is then used as the basis for comparing the two samples.

SUMMARY OF THE INVENTION

The present invention provides a system for transmission loss comparison.

One embodiment of the present invention compares the transmission losses through optical paths through a first solution and a second solution. This embodiment includes first and second light sources for transmitting light through the first and second solutions. Also provided are first and second light detectors corresponding to the first and second light sources, and comparison means for comparing the outputs of the two detectors in order to determine which solution is darker.

In addition, this embodiment includes a common gain balance configuration means for calibrating the relative gain of the two light detectors in order to compensate for signal differences between each source/detector path arising from various mechanical or optical factors. Further included is a dark solution compensation bias to compensate for differences between each source/detector path arising from spectral differences between the two light sources.

In order to stabilize the measurement decision, the system also provides source modulation hysteresis, wherein a feedback path is provided between the output of the comparison means and one of the light sources.

DESCRIPTION OF PREFERRED EMBODIMENTS

Figure 1:
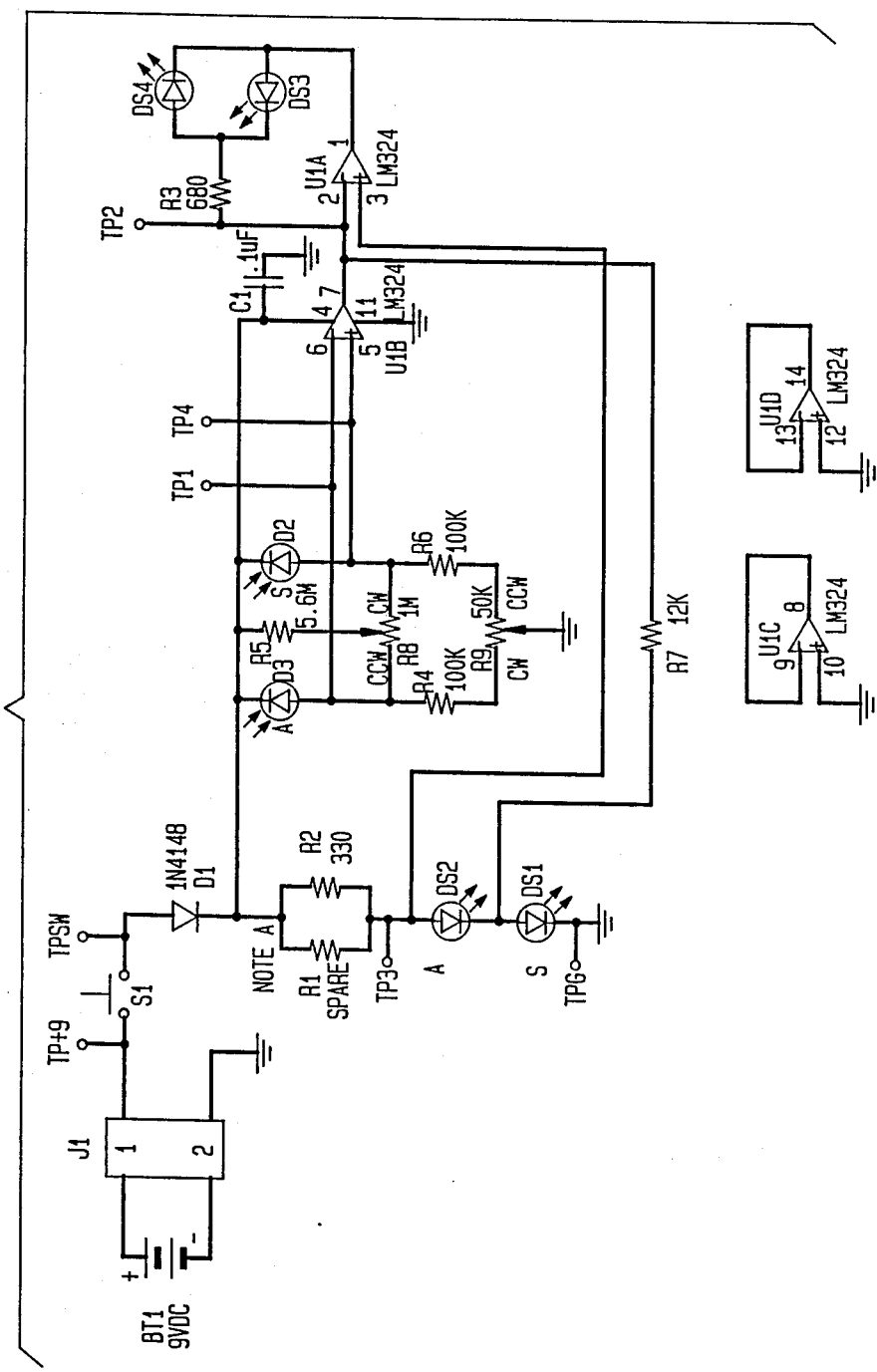
FIG. 1 is a schematic drawing of a preferred embodiment of an electrical circuit according to the present invention.

The invention can be better understood by reference to FIG. 1, which shows a preferred embodiment of an electrical circuit according to the present invention.

The device shown in FIG. 1 compares the darknesses of two solutions: a reference solution A in one test tube, with a known concentration of solute, and a sample S of the same type of solution, but of unknown concentration. As described more fully below, the device accurately determines whether the sample S is a stronger or weaker solution than the reference solution.

In use, the operator actuates pushbutton switch S1, which causes current to flow through the device from battery BT1. Matched light-emitting diodes DS1 and DS2 then transmit light through sample S and reference A, respectively. Light from LED's DS1 and DS2 not absorbed after passing through the tubes and the liquids is focussed on matched detectors D2 and D3. Each detector produces an output current analogous to the amount of light detected. These currents in turn produce voltages across resistors R6, R4 and balance potentiometer R9. In manufacturing tests, these voltages can be measured at test points TP4 and TP1.

The two voltages are compared at op-amp U1B, which is configured as a comparator. Capacitor C1 serves to filter out any signal component in the power supply to op-amp U1. If TP4 is greater than TP1, then comparator U1B will go high, which will provide a positive current through LED DS4 via resistor R3, thus causing LED DS4 to light. It will be seen that TP4 will be greater than TP1 when there is greater current flow through D2 than through D3. This means that more light has reached D2 from DS1 than has reached D3 from DS2, thus indicating that the reference A has absorbed more light than sample S. Thus, the lighting of DS4 indicates that sample S is a weaker concentration of solution than reference A.

If TP1 is greater than TP4, then comparator U1B will go low, and op-amp U1A, also configured as a comparator, will go high, thus producing a positive current flow through LED DS3, causing it to light. It will be seen that TP1 will be greater than TP4 when there is greater current flow through D3 than through D2. This means that more light has reached D3 from DS3 than has reached D2 from DS1, thus indicating that sample S has absorbed more light than reference A. Thus, the lighting of DS3 indicates that sample A is a stronger concentration of solution than reference A.

It will be seen that the detected S current from photodiode D2 flows through resistor R6 and part of potentiometer R9 (from CCW to the wiper) to ground. Similarly, the detected A current from photodiode D3 flows through resistor R4 and the CW side of potentiometer R9 to ground. The position of the wiper on potentiometre R9 is adjusted during manufacture to compensate for overall gain differences between the A and S measurement paths. Potentiometer R9 compensates for optical (mechanical), electro-optic, as well as electrical gain differences. This type of common gain balance configuration is used in other applications.

During manufacture, a variable bi-directional current source is used to inject a periodic triangular waveform into the circuit at TP4. The particular waveform is chosen such that the system just barely flips back and forth between the two indicator states. Potentiometer R9 is adjusted so that the computed average voltage at TP1 equals the computed average voltage at TP4 with clear water in each test tube, i.e., at high signal levels, typically 4 volts at TP1 and TP4. Because the relative gain is adjusted based on the computed average voltage, the result of the calibration is that the A side gain slightly exceeds the S side gain. The difference between the two gains is equal to half of the source modulation hysteresis value, discussed below.

In addition to the gain adjustment provided by potentiometer R9, the present invention includes a novel use of offset current to provide dark solution compensation bias. The offset current flows through resistor R5 and potentiometer R8. The amount of offset current flowing through resistors R4 and R6 depends upon the position of the wiper of potentiometer R8, which acts as a current divider. Further, because photodiodes D2 and D3 possess extremely high impedance, it will be seen that the voltage across resistor R5 depends upon the voltages at TP1 and TP4: the lower the voltages at TP1 and TP4, i.e., the lower the signal level, the greater the voltage across resistor R5, with an associated increase in current flow. Thus, the dark solution compensation bias is greatest at lower signal levels and smallest at higher signal levels. This feature permits the dark solution compensation bias to be used in conjunction with the common gain balance configuration described above.

During manufacture, potentiometer R8 is adjusted at the other end of the dynamic range from that used to adjust potentiometer R9. A dark solution is used that absorbs 97 percent of the light from LED's DS1 and DS2, transmitting only 3 percent. This is an absorbance of 1.5 A. [Absorbance$\equiv -\log_{10}$(transmitted light).] With matched dark solutions in each tube, R8 is adjusted so that the voltage measured at TP1 equalts the voltage measured at TP4. Thus, resistor R5 and potentiometer R8 provide the dark solution bias compensation mentioned above.

As mentioned above, LED's DS1 and DS2 may not have identical spectral output, even though they may have matched overall brightness. Reference solution A and sample solution S may have a relatively narrow absorption peak. If the peak wavelengths of DS1 and DS2 do not match, or if they have mismatched out-of-band energy, then the detected currents in photodiodes D2 and D3 will not stay matched for high absorbance solutions.

The necessity for dark solution bias compensation can be appreciated from the following example: In a system without dark solution bias compensation, if one source has 1 percent of its energy outside of the absorption band of the solution, then the relative gain between the two light detectors can be easily adjusted for a match using clear solutions. However, if a dark solution with 97 percent absorption of in-band energy is introduced into the system for comparison, it will be appreciated that without dark solution bias compensation, there is no attenuation of out-of-band energy, and the original 1 percent out-of-band energy now represents 33 percent of the energy received at the detector. A similar phenomenon occurs if the sources have different peak wavelengths that coincide with a sloping absorbance curve for the solutions under test.

Thus, it will be seen that the dark solution bias compensation possesses several desirable features:

First, there is minimum interaction with gain adjustment. At high signal levels, the voltage across R5 and the bias current are reduced, when compared with low signal levels and maximum voltage across R5.

Second, there is minimum interaction with detector load impedance levels. The bias impedance stays high, relative to detector loads R4 and R6.

This, the gain adjustment will properly adjust dark compensation bias. The use of offset currents permits the adjustment for spectral differences using a different mechanism from that used to adjust for differences arising from miscellaneous mechanical factors. The system behaves as though the sources were exactly matched for spectral content. This greatly simplifies the calibration procedure.

Returning now to comparators U1A and U1B: As discussed above, comparator U1B decides which voltage is higher, TP1 or TP4. Comparator U1A is connected as an inverter, using the anode voltage of LED DS2 as a logic threshold voltage. Indicator LED's DS3 and DS4 are connected back-to-back and are driven differentially. This insures that they will not be on at the same time, and also minimizes the part count, as only one drive resistor is required.

An important part of the circuit is feedback resistor R7. The comparator feedback to LED DS1 via feedback resistor R7 is the source modulation hysteresis mentioned above.

When TP4 is slightly higher than TP1, output pin 7 of comparator U1B will start to go from low to high. As it does so, current flows through feedback resistor R7, increasing the brightness of LED DS1, which in turn produces positive feedback at TP4 of approximately 3½ percent, thereby stabilizing the system. The increase in brightness at LED DS1 is approximately linear with current at the operating point established by R1 and R2. The values shown in FIG. 1 provide a current increase of 0.035 percent, which corresponds to an equivalent absorbance change of 0.015 A.

In operation, the hysteresis operates as follows: Assume that the sample solution S is darker than reference solution A. TP4 should be less than TP1. However, further assume that, because of some transient state, TP4 is actually greater than TP1. Feedback through resistor R7 causes more current to flow through LED DS1, causing it to become brighter. As the solutions return to their normal state, TP1 will start to drop until it becomes lower than TP4. When that happens, the output of comparator U1B will drop. Because of the feedback path through resistor R7, the current through LED DS1 will also drop, causing it to become dimmer. The net result is to stabilize the circuit by minimizing the number of transitions between indicator states.

Source modulation hysteresis provides a significant improvement over normal voltage feedback hysteresis. With source modulation hysteresis, the hysteresis is constant in absorbance units (equivalent to dB), throughout the dynamic range of the instrument. This results in a well-behaved system, that is not twitchy or overly senstive for clear solutions nor insensitive for dark solutions, as is the case using normal voltage feedback. Source modulation hysteresis yields stable readings, even though the tubes may exhibit slight scratches, or move slightly in the sleeves (optical path), or the instrument may be jiggled during measurement.

It should be noted that other configurations of the circuit would be within the spirit of the invention. For example, the polarity of the feedback can be changed from positive to negative. This changes the circuit to an oscillator, if the sample solution S and the reference solution A are close to the same concentrations. By adjusting the feedback, the circuit can be used as a window detector. Since the feedback is constant in percentage at the source, the window will be constant in absorbance units over the entire measurement range of the instrument. With slight additional circuitry, such as a ramp generator, the window comparator provides a variable duty cycle indicator, and shows how far apart the solutions are, i.e., through variable duty cycle blink rates on the indicator LED's.

Preferred components for use in the circuit are set forth in Table I. Table II sets forth the specifications required for LED's DS1 and DS2 and photodiodes D2 and D3:

TABLE I

| # | DESCRIPTION | PER BOARD | REF. DESIGNATOR |
|---|---|---|---|
| 1 | CAP,.01 uF 20% SOV MONO. CERAMIC .1" LS AVX #SR205E103MAA NIC #NCM20Z5U103M500 | 1 | C1 |
| 2 | RES, CARB. FLM. ohm 5% ¼ W | 1 | R1 (spare) |
| 3 | RES, CARB FLM 240,330/470 ohm 5% ¼ W | 1 | R2 (match w/DS1&2) |
| 4 | RES, CARB. FLM. 680 ohm 5% ¼ W | 1 | R3 |
| 5 | RES, CARB. FLM. 12K ohm 5% ¼ W | 1 | R7 |
| 6 | RES, CARB. FLM. 100K ohm 5% ¼ W | 2 | R4,6 |
| 7 | RES, CARB. FLM. 5.6 M ohm 5% ¼ W | 1 | R5 |
| 8 | POT, 50K ohm ⅜" SQ. CERMET/SEALED LAYDOWN BOURNS #3386P-1-503 VRN #780-12P-50K | 1 | R9 |
| 7 | POT, 1 M ohm ⅜" SQ. CERMET/SEALED LAYDOWN BOURNS #3386P-1-105 VRN #780-12P-1M | 1 | R8 |
| 10 | DIODE, 1N4148 | 1 | D1 |
| 11 | PHOTODIODE #TELEFUNKEN #BPW 46 (PIN) SCREENED TO CSPDOIT | 2 | D2,3 } SEE MEMO 1M61021 A |
| 12 | LED RED #CSRD20T T-1 ¾ 100 mc STANLEY #ESBR5501 or #5701 SCREENED TO CSRD20T | 2 | DS1,DS2 |
| 13 | LED RED T-1,3mc LITE ON #LTL-4221 LUMEX #SSL-LX3054ID | 2 | DS3,DS4 |
| 14 | IC LM324 (or CS224B) | 1 | U1 |
| 15 | CONN, BATTERY SNAP MOUSER #12BC421 | 1 | J1 |
| 16 | SWITCH, SPST ITT Schadow #KSA-OM-221 OR #KSA-OA-221 | 1 | SW1 |
| 17 | BATTERY, 9V CARBON | 1 | BATT |
| 18 | PCB, CSI #1682 REV.B | 1 | PCB |
|  | CASE COMPONENTS |  |  |
| 19 | CASE, FRONT w/printing | 1 | SANTIN ENGINEERING |
| 20 | CASE, REAR | 1 | SANTIN ENGINEERING |
| 21 | CASE, TOP | 1 | SANTIN ENGINEERING |
| 22 | SLEEVE-HALF, TUBE | 4 | SANTIN ENGINEERING |
| 23 | WINDOW/LENS, MOLDED | 4 | SANTIN ENGINEERING |
| 24 | CAP, SWITCH BUTTON | 1 | SANTIN ENGINEERING |
| 25 | SPACER, SWITCH BUTTON | 1 | SANTIN ENGINEERING |
| 26 | SPACER, LED | 1 | SANTIN ENGINEERING |
| 27 | FOAM INSERT, BATTERY | 1 | GREEN RUBBER |
| 28 | FOAM INSERT, COVER | 1 | GREEN RUBBER |
| 29 | LABEL, INSTRUCTIONS/SERIAL NUMBER | 1 | TECHPRINT |
| 30 | LABEL, "OK" | 1 | AMHERST LABEL |
| 31 | SCREW, #6 × .5" PH. PAN HD.TYPE-B BLUNT PT. STEEL ZINC PLATED | 4 |  |
| 32 | SCREW, #2 × ¼" PH. PAN TYPE "25" STEEL ZINC PLATED | 8 |  |
|  | PACKAGING |  |  |
| 33 | FOAM, .125 × 4.625 × 9.125 IN. | 1 |  |
| 34 | BOX, 200# DIE CUT 1PC. FOLDER | 1 | HORN CORP. |
| 35 | TAPE, 2" CLEAR PVC QTY = ROLL | .005 |  |

TABLE II

SPECIFICATIONS FOR LED'S DS1, DS2
CSRD20T - MATCHED PAIR
(SIMILAR TO H.P.HLMP-3750)

| LED ULTRABRIGHT RED T-(1¾) | |
|---|---|
| PEAK | $650 \pm 20$ nm |
| $I_V$ @ 10 ma | 80 mcd (min) |
| $V_F$ @ 10 ma | 2.3 V (max) @ 25° C. |
| VIEWING ANGLE | $\leq 25°$ |
| $I_V$ FLATNESS vs ANGLE | TO BE DETERMINE |
| TEMP RANGE - OPERATING | 10° TO 35° C. |
| TEMP RANGE - STORAGE | $-20°$ TO 70° C. |

LINEARITY MATCHING

| $1 \text{ ma} \leq I_F \leq 10 \text{ ma}$ | $I_{V1} = KI_{V2} \pm 2\%$ |
|---|---|

BRIGHTNESS MATCHING

| @ $I_F = 5$ ma | $\pm 15\%$ max |
|---|---|

TABLE II-continued

PEAK WAVELENGTH MATCHING:
@ $I_F = 5$ ma  W = wavelength

| FOR $W_{peak}$ 640 TO 660 | $W_1 = W_2 \pm 7$ nm |
|---|---|
| FOR $W_{peak}$ 660 TO 670 | $W_1 = W_2 \pm 5$ nm |
| FOR $W_{peak}$ 670 TO 685 | $W_1 = W_2 \pm 2$ nm |

OUT OF BAND ENERGY MATCHING:

% OF TOTAL EMITTED ENERGY OUTSIDE 600 TO 700 nm MUST MATCH WITHIN ±0.2% OF TOTAL ENERGY.

SPECIFICATIONS FOR PHOTODIODES D2,D3
CSPDOIT - MATCHED PAIR

PHOTODIODE
TO-18, TO-92, OR T-(1¾)CASE
(SIMILAR TO SIEMENS#SFH206K)

| PHOTO SENS. @ 650 nm | | |
|---|---|---|
| $V_R = 8$ V | | |
| $E_\sigma = 0.5$ mw/cm$^2$ | | 35 μa min |
| RADIANT SENS AREA | | 5 mm$^2$ min. |
| VIEWING ANGLE | | 60° min. |
| DARK CURRENT @8 V 25° | | 3 na max. |

LINEARITY MATCHING

| $0.1 \text{ μa} \leq I_p \leq 10 \text{ μa}$ | $I_{p1} = KI_{p2} \pm 1\%$ |
|---|---|
| SENS. MATCHING | $I_{p1} = I_{p2} \pm 15\%$ |

TABLE II-continued

| TEMP RANGE - OPERATING | 10° TO 35° C. |
|---|---|
| TEMP RANGE - STORAGE | −20° to 70° C. |

Figure 2:
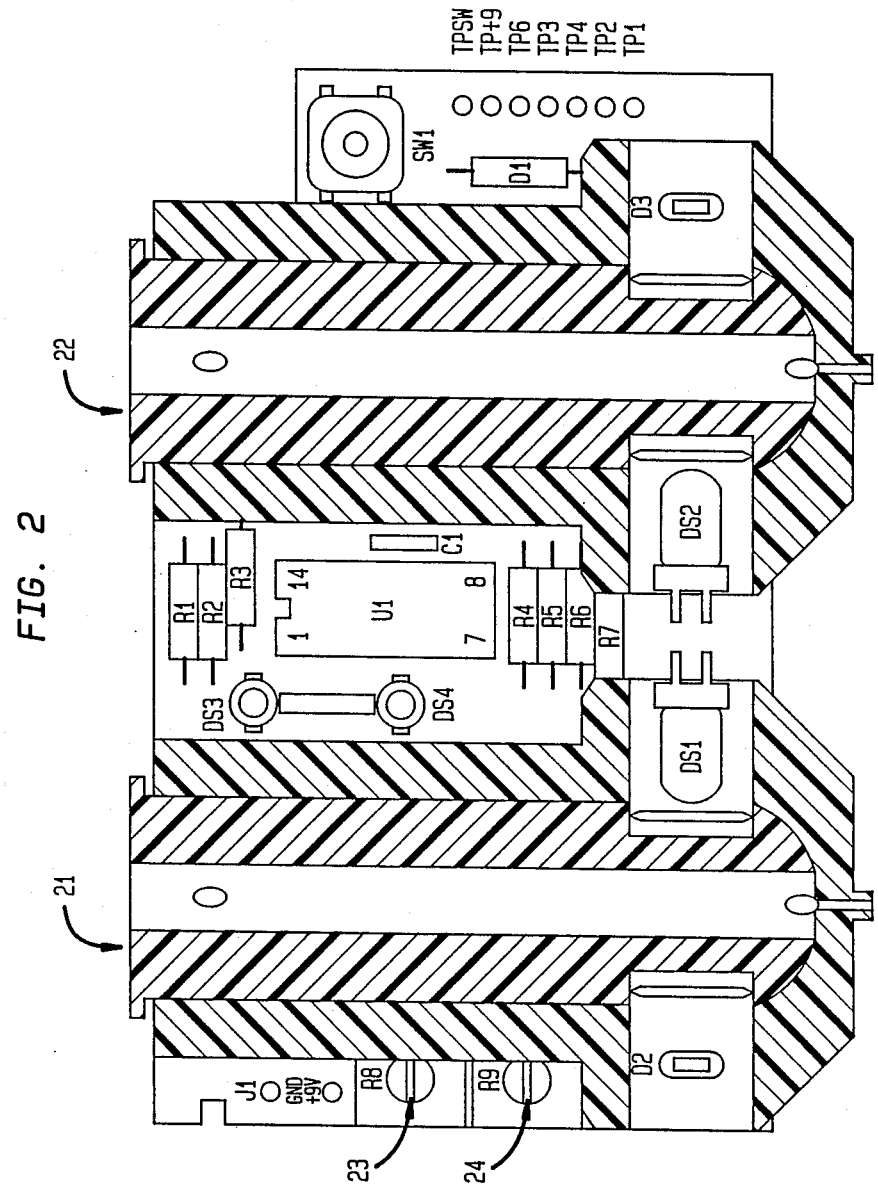
FIG. 2 is a schematic drawing of a preferred embodiment of a mechanical arrangement of the preferred embodiment of FIG. 1.

FIG. 2 is a schematic drawing of a preferred embodiment of a mechanical arrangement of the preferred embodiment of FIG. 1. Sleeves 21 and 22, shown in cross section, are used to hold test tubes containing respectively sample solution S and reference solution A. It is contemplated that when the two test tubes are inserted that the sleeves are sufficiently opaque to prevent ambient light conditions from adversely affecting the accuracy of the comparison. Adjustment of potentiometers R8 and R9 is accomplished through centered screw slots 23 and 24.

What is claimed is:

1. A system for determining relative transmission loss over a reference path and a sample path, the system comprising:
   reference and sample transmitters, each having an output signal and a transfer characteristic, transmitting over reference and sample paths respectively, to reference and sample receivers respectively, each receiver having a signal output;
   comparison means, having an output, and having a pair of inputs connected to the outputs of the reference and sample receivers, for comparing the outputs of the reference and sample receivers;
   each associated transmitter, path, and receiver constituting collectively a channel, the system therefore having a reference channel and a sample channel, each channel having a gain, the system further comprising:
   gain balance means for adjusting the relative gains of the reference and sample means over a first dynamic range, wherein there is relatively little transmission loss, and over a second dynamic range, wherein there is substantial transmission loss, so as to compensate for differences in the waveform characteristics of the signals generated by the reference and sample transmitters.

2. A system according to claim 1, wherein the reference and sample transmitters have transfer characteristics that are substantially matched over their entire dynamic ranges.

3. A system according to claim 2, wherein the gain balance means further includes voltage calibration means for calibrating the relative voltage levels of the output signals of the receivers while matched transmission loss conditions in the first dynamic range are presented to the receivers.

4. A system according to claim 3, wherein the voltage calibration means comprises a potentiometer-resistor network connected to the receivers in a voltage divider configuration, such that adjusting the position of the wiper on the potentiometer affects the relative levels of the output signals from the receivers.

5. A system according to claim 1, wherein the transmitters are light sources and the paths are optical.

6. A system according to claim 2, wherein the transmitters are light sources and the paths are optical.

7. A system according to claim 3, wherein the transmitters are light sources and the paths are optical.

8. A system according to claim 4, wherein the transmitters are light sources and the paths are optical.

9. A system according to claim 2, wherein the gain balance means further includes current offset calibration means for calibrating the relative current levels of the output signals from the receivers while matched transmission loss conditions in the second dynamic range are presented to the receivers.

10. A system according to claim 9, wherein the current offset means comprises a potentiometer-resistor network connected to the receivers in a current divider configuration, such that adjusting the position of the wiper on the potentiometer affects the relative amount of current of the output signals from the receivers.

11. A system according to claim 9, wherein the transmitters are light sources and the paths are optical.

12. A system according to claim 10, wherein the transmitters are light sources and the paths are optical.

13. A system for determining relative transmission loss over a reference path and a sample path, the system comprising:
   reference and sample transmitters, each having an output signal and a transfer characteristic, transmitting over reference and sample paths respectively, to reference and sample receivers respectively, each receiver having a signal output;
   comparison means, having an output, and having a pair of inputs connected to the outputs of the reference and sample receivers, for comparing the outputs of the reference and sample receivers, for comparing the outputs of the reference and sample receivers;
   each associated transmitter, path, and receiver constituting collectively a channel, the system therefore having a reference channel and a sample channel, each channel having a gain, the system further comprising:
   voltage gain calibration means for calibrating the relative gains of the reference and sample means over a first dynamic range, in which there is relatively little transmission loss; and
   current offset calibration means for calibrating the relative gains of the reference and sample means over a second dynamic range, in which there is substantial transmission loss;
   the voltage gain calibration means and the current offset calibration means compensating for differences in the waveform characteristics of the signals generated by the reference and sample transmitters.

14. A system according to claim 13, wherein the transmitters are light sources and the paths are optical.

15. A system for determining relative transmission loss over a reference path and a sample path, the system comprising:
   reference and sample transmitters, each having an output signal and a transfer characteristic, transmitting over reference and sample paths respectively, to reference and sample receivers respectively, each receiver having a signal output;
   comparison means having a pair of inputs connected to the outputs of the reference and sample receivers, for comparing the outputs of the reference and sample receivers, and for generating as an output indicator states that are indicative of the result of the comparison;
   each associated transmitter, path and receiver constituting collectively a channel, the system therefore having a reference channel and a sample channel, each channel having a gain, the system further comprising:

source modulation hysteresis means for minimizing the number of transitions between indicator states, the source modulation hysteresis means comprising a positive feedback path between the comparison means output and the sample transmitter, such that when the comparison means output indicates that the sample path displays less transmission loss than the reference path, the sample transmitter output is increased, thereby increasing the difference between the outputs of the reference and sample receivers.

16. A system according to claim 15, wherein the source modulation hysteresis means includes a feedback resistor of a value to produce positive feedback to the sample transmitter output of approximately 3½ percent.

17. A system according to claim 15, wherein the transmitters are light sources and the paths are optical.

18. A system according to claim 16, wherein the transmitters are light sources and the paths are optical.

* * * * *